United States Patent [19]
Rydell et al.

[11] Patent Number: 5,171,311
[45] Date of Patent: Dec. 15, 1992

[54] PERCUTANEOUS LAPAROSCOPIC CHOLECYSTECTOMY INSTRUMENT

[75] Inventors: Mark A. Rydell, Golden Valley; David J. Parins, Columbia Heights; Steven W. Berhow, Brooklyn Center, all of Minn.

[73] Assignee: Everest Medical Corporation, Minneapolis, Minn.

[21] Appl. No.: 763,559

[22] Filed: Sep. 23, 1991

Related U.S. Application Data

[62] Division of Ser. No. 516,740, Apr. 30, 1990, Pat. No. 5,071,419.

[51] Int. Cl.⁵ ............................................. A61B 17/39
[52] U.S. Cl. ........................................ 606/48; 606/50; 604/35
[58] Field of Search ............... 606/45, 46, 48, 49, 606/50; 604/35

[56] References Cited

U.S. PATENT DOCUMENTS

| | | | |
|---|---|---|---|
| 1,814,791 | 7/1931 | Ende | 606/50 |
| 2,275,167 | 3/1942 | Bierman | 606/50 X |
| 4,161,950 | 7/1979 | Doss et al. | 606/50 X |
| 4,532,924 | 8/1985 | Auth et al. | 606/50 |
| 5,007,908 | 4/1991 | Rydell | 606/50 X |
| 5,013,312 | 5/1991 | Parins et al. | 606/50 X |

*Primary Examiner*—Lee S. Cohen
*Attorney, Agent, or Firm*—Haugen and Nikolai

[57] ABSTRACT

An instrument for performing a percutaneous laparoscopic cholecystectomy includes a generally rigid, tubular body with a proximal end, a distal end and a lumen extending between these two ends and with a pair of bipolar electrodes projecting from the distal end of the tubular body and a handle member affixed to its proximal end. The outside diameter of the tubular body is sufficiently small that it can readily pass through a cannula inserted through a puncture made through the abdominal wall. A pair of conductors, connected at one end to the bipolar electrodes and at their other end to a source of radio frequency voltage, extend through the tube's lumen and a handle. Moreover, a fluid port may be formed through the handle so as to be in fluid communication with the lumen of the tube whereby fluids may be perfused through the instrument during its use or a suction may be applied to the proximal port for aspirating the surgical site. In one embodiment of the invention, the bipolar electrodes may be formed as conductive traces extending along the peripheral edges of a thin ceramic blade. In an alternative arrangement, the bipolar electrodes comprise first and second closley space J-spaced conductive hook members.

3 Claims, 1 Drawing Sheet

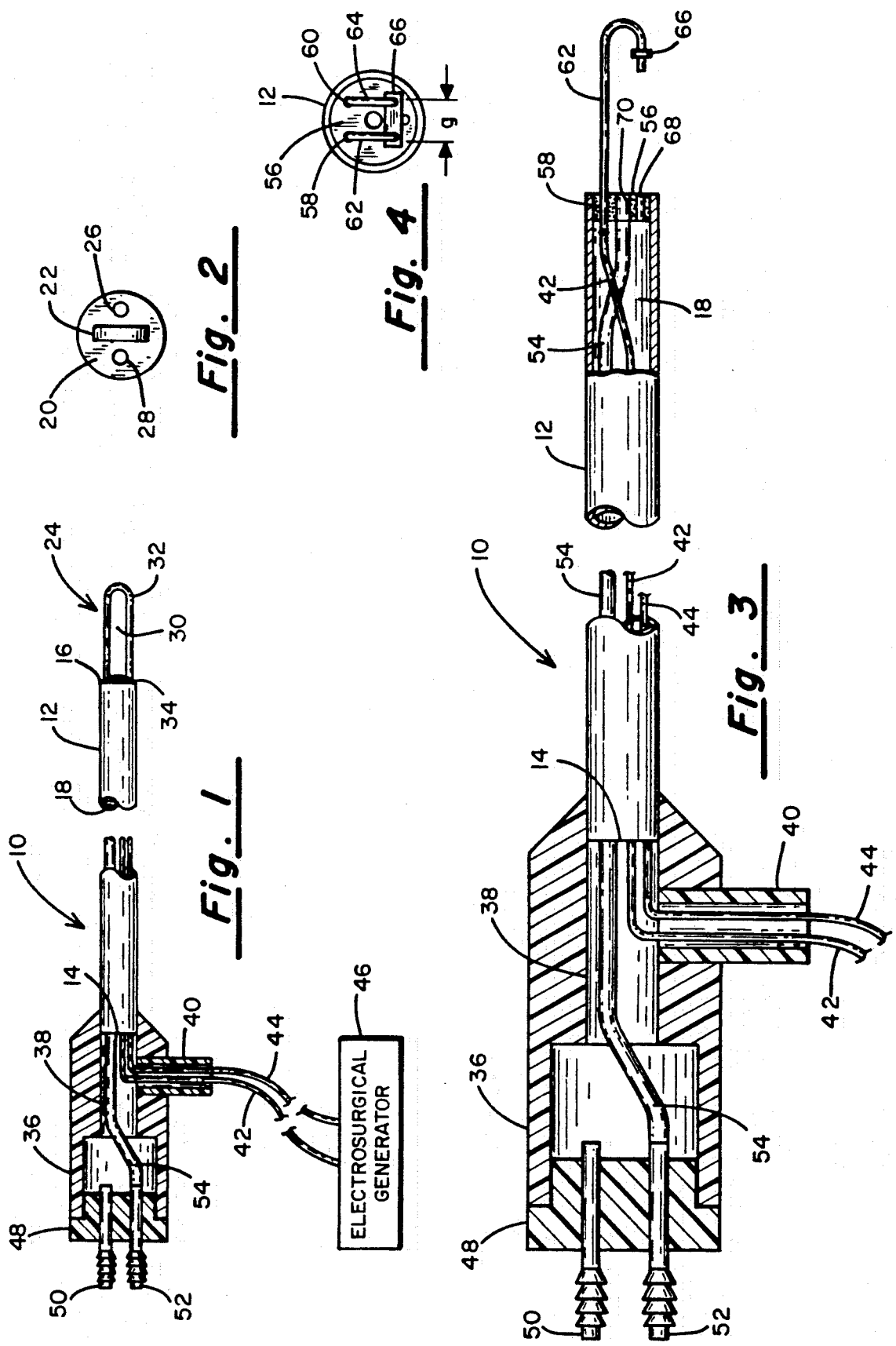

PERCUTANEOUS LAPAROSCOPIC CHOLECYSTECTOMY INSTRUMENT

This is a divisional of copending application Ser. No. 07/516,740, filed on Apr. 30, 1990, now U.S. Pat. No. 5,071,419.

BACKGROUND OF THE INVENTION

1. Field of the Invention

This invention relates generally to electrosurgical instruments, and more particularly to a bipolar electrosurgical cutting instrument specifically designed for use in the performance of percutaneous laparoscopic cholecystectomy procedures.

2. Discussion of the Prior Art

The conventional treatment for a diseased gallbladder has been a total cholecystectomy involving cutting a fairly large incision through the abdominal wall and, using a scalpel, to dissect the gallbladder from its bed and to cut the cystic artery and cystic duct to thereby release the organ and allow it to be extracted through the incision. According to *National Inpatient Profile*, Healthcare Knowledge Systems, Ann Arbor, Mich., 1989:360, the average postoperative stay following gallbladder removal surgery of this type in 1988, on a nationwide basis, was 6.1 days and full recovery to normal activities required four to six weeks recuperation.

A relatively new procedure referred to as "laparoscopic laser cholecystectomy" has been devised and it is significantly less invasive than the heretofore conventional approach for gallbladder removal. Rather than working through a major incision in the abdominal wall, a first small puncture would is made in the umbilicus. A needle is inserted and a pneumoperitoneum is established with $CO_2$ gas to distend the abdomen. Next, a trocar and cannula are inserted through the umbilical incision and following removal of the trocar, a 10 mm, 0° diagnostic laparoscope is inserted. Rather than direct visualization through the laparoscope, the scene may be viewed on a CRT screen.

Upon proper observation of the peritoneal cavity, three additional stab incisions are made at predetermined locations and cannulas are inserted. Two of the cannulas may be 5 mm in diameter and the other, 11 mm. The lumens in the cannulas are sufficiently large to permit surgical instruments to be inserted therethrough, the instruments including a grasping forceps, a clip applier for ligating the cystic duct and cystic artery and a microscissors. A flexible, fiber-optic rod coupled to the output of a laser is used to effect hemostatic cutting and vaporization.

While non-contact positioning of the laser fiber may be used for coagulation if hemorrhage occurs, in the event that the bleeder is larger than can be controlled with the laser in its non-contact mode, monopolar cautery is used, with the electrosurgical instrument being inserted through one of the cannulas.

The percutaneous laparoscopic cholecystectomy procedure allows total removal of the gallbladder through the larger cannula and following the surgery, a single stitch in the umbilicus and the use of sterile adhesive strips for closing the other three wounds is all that is required. Using this procedure, the hospital stay has been reduced to less than one day and the period for total recovery and resumption of normal activities is reduced to about four days. Moreover, scarring is minimal.

OBJECTS

The present invention is directed to a bipolar electrosurgical instrument which is specifically designed to be insertable through a cannula for use in dissection of the gallbladder from the internal organs to which it attaches and which may also be used for coagulating and cauterizing as the need arises during the laparoscopic cholecystectomy procedure. Thus, the more expensive laser surgical instrument can be dispensed with and replaced with a disposable low-cost substitute.

It is accordingly a principal object of the present invention to provide an improved instrument for carrying out laparoscopic surgical procedures with the abdominal cavity.

Another object of the invention is to provide an improved electrosurgical instrument for performing laparoscopic cholecystectomy.

Yet another object of the invention is to provide a bipolar electrosurgical instrument allowing better control over the location where cutting is intended than can be achieved with monopolar electrosurgical instruments.

SUMMARY OF THE INVENTION

The foregoing features, objects and advantages of the present invention are attained by providing an electrosurgical instrument comprising a generally rigid tube having a proximal end, a distal end and a lumen extending from the proximal end to the distal end where the outside diameter of the tube is sufficiently small to permit it to be passed through a cannula percutaneously positioned through the abdominal wall. The length of the rigid tube is sufficient to permit bipolar electrodes affixed to the distal end thereof to reach the internal organ to be surgically treated when the instrument is inserted through the cannula. The bipolar electrodes are spaced from one another by a predetermined small gap and first and second conductors, each being insulated from the other are extended through the lumen of the rigid tube to connect to the bipolar electrodes. A molded plastic hub is affixed to the proximal end of the rigid tube and associated with the hub are electrical connector means especially adapted to permit a source of RF power to be applied via the insulated conductors to the bipolar electrodes.

In a first embodiment of the invention, the bipolar electrodes comprise printed traces of a conductive material formed along the peripheral edge of an insulating substrate so that the gap comprises the thickness dimension of the substrate. In an alternative embodiment, the electrodes comprise two separate J-shaped conductive wire hooks which project outwardly from the distal end of the rigid tube in a side-by-side relationship and which are suitably spaced by a ceramic insulator coupled between the free ends of the hooks. This latter arrangement affords the ability of the surgeon to apply traction to the organ being dissected as RF power is applied to create an arc between the spaced electrodes, the arc being used to effect the cutting. The application of lower power can be used to supply the requisite heat energy for electrocautery for coagulation.

DESCRIPTION OF THE DRAWINGS

The foregoing features, objects and advantages of the invention will become apparent to those skilled in the art from the following detailed description of a preferred embodiment, especially when considered in conjunction with the accompanying in which like numerals in the several views refer to corresponding parts.

FIG. 1 is a partially sectioned, side elevation of a bipolar surgical instrument configured in accordance with a first embodiment of the invention.

FIG. 2 is a distal end view of the instrument of FIG. 1;

FIG. 3 is a partially sectioned, side elevational view of a second embodiment of the invention; and FIG. 4 is a distal end view of the instrument of FIG. 3.

DESCRIPTION OF THE PREFERRED EMBODIMENT

Referring first to FIG. 1, there is indicated generally by numeral 10 an electrosurgical instrument specifically designed for use in percutaneous laparoscopic cholecystectomy surgical procedures. It is seen to comprise an elongated, rigid tubular member 12 which may be formed from a variety of materials including plastics and metals, with stainless steel perhaps being preferred. The tube 12, if fabricated from stainless steel, may comprise six gauge tubular stock having an outside diameter of 0.205 inches and an internal diameter of 0.173 inches. Moreover, it is preferably blackened over its surface so as to be non-light reflective. The tube 12 has a proximal end 14, a distal end 16 and a lumen 18 extending the entire length thereof.

Fitted into the distal end 16 of the rigid tube 12 is a plug member 20 (FIG. 2) which may be formed from a high temperature plastic, such as medical grade polysulfone or a ceramic. The plug 20 includes a narrow slot 22 for receiving the proximal end of an electrosurgical blade 24 and a pair of apertures 26 and 28, the purpose of which will be described hereinbelow.

The blade 24 preferably comprises a thin ceramic substrate 30 having a pattern of conductive traces as at 32 screened thereon. Ceramics, such as aluminum nitride and silicon nitride, have proved to be useful in this application. Specifically, the conductive traces extend around the perimeter of the substrate 30 on opposed side surfaces thereof and are spaced from one another by the thickness dimension of the substrate. This thickness dimension may, typically, be 0.025 inches, but no limitation to that particular dimension is intended. High temperature epoxy may be used to tightly secure the blade 24 in the slot formed in the plug 20 and fastened to the distal end of the rigid tube 12.

With continued reference to FIG. 1, it can be seen that there is affixed to the proximal end 14 of the tube 12 a molded plastic hub 36 having a bore 38 formed longitudinally therethrough into which the proximal end portion 14 of the tube 12 is inserted and adhesively bonded. Communicating with the bore 38 is a side port 40 in the form of a tubular flexible reinforcement or strain relief member through which a pair of insulated conductors 42 and 44 leading to an electrosurgical generator 46 extend. (The electrosurgical generator is preferably of the type described in the Stasz U.S. Pat. No. 4,903,696. The conductors pass through the lumen 18 of the rigid tube 12 and are individually connected to the conductive traces 32 formed on the opposed side surfaces of the blade substrate 30.

Fitted into the proximal end of the hub 36 is a molded plastic plug 48 into which is fitted a pair of tubular barb couplers 50 and 52. The barb coupler 50 is in fluid communication with the bore 38 and, hence, the lumen 18 of the tube 12. When a source of vacuum is joined to the barb coupler 50, via appropriate tubing, fluids can be aspirated through the distal bore or port 26 formed in the plug 20.

A tube 54 is secured to the distal end of the barb coupler 52 and that tube 54 extends through the bore 38 and the lumen 18, reaching the distal port 28 in the plug 20. The barb coupler 52 is adapted to be coupled to a further tube (not shown) leading to a source of flushing liquid, e.g., saline, which allows the flushing liquid to be perfused through the instrument and out its distal port 28.

In use, the instrument of FIG. 1 will have its tubular portion 12 inserted through the lumen of a cannula which extends through a puncture formed in the abdominal wall. While viewing the surgical site, via a laparoscope, the surgeon may cause the RF power generated by the electrosurgical generator 46 to be applied across the gap defined by the thickness of the substrate 30 such that when tissue to be dissected is contacted by the blade, an arc will be developed across the gap sufficient to effect cutting. When blood or other body fluids obscure the laparoscopic view of the surgical site, a flushing liquid can be injected through the coupler 52 and through the tube 54 to exit the port 28 while a vacuum is applied, via barbed coupler 50, to allow the flushing liquid and blood to be removed. When it is desired to coagulate, the same instrument may be used, but with a lower power setting of the electrosurgical generator 46.

The length of the tubular member 12 is made sufficient to allow the blade 24 to reach the appropriate location within the abdomen when the instrument is inserted through its cannula. The hub or handle member 36 permits the instrument to be readily gripped to facilitate manipulation of the cutting blade 24 relative to the tissue to be dissected.

Referring next to FIGS. 3 and 4, an alternative embodiment of the present invention will now be explained. The embodiment of FIGS. 3 and 4 differs from that of FIGS. 1 and 2 principally in the configuration of the distal plug and the electrode structures used in each. In the arrangement of FIG. 3, rather than including a slot as at 22 in FIG. 2, the plug 56 includes a pair of closely spaced apertures 58 and 60 through which J-shaped hook electrodes 62 and 64 project. That is to say, the electrodes are formed of wire and the shank of the hook electrode 62 passes through an aperture or bore 58 while the shank of the hook electrode 64 fits through the bore 60 in the plug 56. The elongated conductors 42 and 44 individually connect to the proximal ends of the hook electrodes 62 and 64 within the confines of the lumen 18 of the tube 12.

A preferred spacing for the gap, g, between the electrodes 62 and 64 may be 0.015 inches and can be maintained by utilizing a rigid ceramic spacer bar as at 66 positioned a short predetermined distance (0.020–0.030 inches) from the free ends of the hook electrode 62 and 64 The electrodes themselves may comprise 0.014 wires. Using this approach, the portions of the electrodes 62 and 64 extending beyond the spacer 66 can be used to initiate cutting when made to pierce into the tissue to be dissected. The rounded end portions of the hook electrodes can also be made to abut tissue so as to cut, on-end, similar to an electrosurgical blade. If blade-like cutting is required, the contacting of the outer curved portion of the hook loop with the tissue is found to produce similar results. Because of the manner in which the electrode wires are bent as a hook, the instrument can be used to apply traction to the tissue as it is being cut. That is to say, the connective tissue may be hooked and put under tension while being cut off. The pulling motion is somewhat easier to control through a laparoscope or cannula than a side-to-side motion which the blade utilizes. This is especially advantageous when it becomes necessary to lift or reposition the gallbladder or other organ during the cutting process.

As with the embodiment of FIGS. 1 and 2, the plug 56 includes an aspiration port 68 and a flushing port 70.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. An electrosurgical instrument for performing laparoscopic procedures comprising:
   (a) a generally rigid tube having a proximal end, a distal end, lumen means extending from said proximal end to said distal end for allowing passage of fluids therethrough, said tube having an outside diameter of a size allowing passage through a cannula and of a length sufficient to reach the internal tissue to be excised when said tube is inserted through the abdominal wall via said cannula;
   (b) a blade member affixed to said distal end of said tube, said blade member comprising a flat insulating substrate having a peripheral edge and first and second major surfaces with a conductive trace extending along at least a portion of said peripheral edge on said first and second major surfaces, the conductive trace on said first major surface being spaced from the conductive trace on said second major surface by a gap corresponding to the thickness of said flat substrate at said portion of said peripheral edge;
   (c) first and second conductors insulated from one another and extending through said lumen means, said first and second conductors being individually connected at one end to said conductive traces on said first and second major surfaces;
   (d) a hub member affixed to said proximal end of said tube, said hub member including at least one passage in fluid communication with said lumen means; and
   (e) means connected to said first and second conductors for connecting said first and second conductors to a source of RF voltage such that a high intensity field is created in said gap effective to cut through said tissue.

2. The electrosurgical instrument as in claim 1 and further including a second lumen means extending the length of said tube and said hub member includes a second passage in fluid communication with said second lumen means.

3. A bipolar electrosurgical instrument for performing laparoscopic cholecystectomy comprising:
   (a) a generally rigid tubular member having a proximal end and a distal end and a first lumen extending from said proximal end to said distal end, the outside diameter of said tubular member being sufficiently small to pass through a cannula;
   (b) a blade member affixed to said distal end of said tubular member, said blade member comprising a thin elongated, narrow substrate having a peripheral edge and first and second major surfaces with a conductive trace extending along at least a portion of said peripheral edge on said first and second major surfaces, the conductive trace on said first major surface being spaced from the conductive trace on said second major surface by the thickness of said thin substrate at said portion of said peripheral edge;
   (c) a handle member secured to said proximal end of said rigid tubular member, said handle member including first and second passages communicating with said first lumen;
   (d) conductor means extending through said first passage and said lumen for coupling a source of RF voltage across said conductive traces on said first and second major surfaces; and
   (e) means for coupling a vacuum to said second passage.

* * * * *